United States Patent
Koley

(10) Patent No.: US 8,580,099 B2
(45) Date of Patent: Nov. 12, 2013

(54) INN NANOWIRE BASED MULTIFUNCTIONAL NANOCANTILEVER SENSORS

(75) Inventor: Goutam Koley, North Augusta, SC (US)

(73) Assignee: University of South Carolina, Columbia, SC (US)

( * ) Notice: Subject to any disclaimer, the term of this patent is extended or adjusted under 35 U.S.C. 154(b) by 73 days.

(21) Appl. No.: 13/237,424

(22) Filed: Sep. 20, 2011

(65) Prior Publication Data

US 2012/0068156 A1    Mar. 22, 2012

Related U.S. Application Data

(60) Provisional application No. 61/384,432, filed on Sep. 20, 2010.

(51) Int. Cl.
    *B03C 5/02* (2006.01)
(52) U.S. Cl.
    USPC .......................................................... 204/667
(58) Field of Classification Search
    USPC ...................... 257/14, 305, E29.168; 204/667
    See application file for complete search history.

(56) References Cited

U.S. PATENT DOCUMENTS

| | | | | |
|---|---|---|---|---|
| 7,462,270 B2 * | 12/2008 | Naughton | ...................... | 205/104 |
| 7,547,881 B2 * | 6/2009 | Hunt et al. | ...................... | 250/305 |
| 7,566,364 B2 * | 7/2009 | Xianyu et al. | ................... | 117/84 |
| 7,609,432 B2 * | 10/2009 | Kamins et al. | ............. | 359/223.1 |
| 2004/0113621 A1 * | 6/2004 | Naughton | ...................... | 324/321 |
| 2005/0241375 A1 * | 11/2005 | Naughton | ........................ | 73/105 |
| 2007/0158766 A1 * | 7/2007 | Lieber et al. | ................... | 257/414 |
| 2007/0235340 A1 * | 10/2007 | Naughton | ...................... | 204/667 |
| 2009/0072137 A1 * | 3/2009 | Hunt et al. | ...................... | 250/305 |
| 2011/0317325 A1 * | 12/2011 | Espinosa et al. | ............. | 361/211 |
| 2012/0036919 A1 * | 2/2012 | Kamins et al. | ............... | 73/31.05 |

OTHER PUBLICATIONS

Ilic, B. et al. "Attogram detection using nanoelectromechanical oscillators". Journal of Applied Physics 2004, 95, 3694-3703.
Yang, Y.T. et al. "Zeptogram-scale nanomechanical mass sensing". Nano Letters 2006, 6(4), 683-686.
Mamin, H.J. et al. "Sub-attonewton force detection at millikelvin temperatures". Applied Physics Letters 2001, 79, 3358-3360.
Fon, W. C. et al. "Nanosclae, phonon-coupled calorimetry with sub-attojoule/Kelvin resolution". Nano letters 2005, 5, 1968-1971.
Huang, X. M. H. et al. Nanomechanical hydrogen sensing. Applied Physics Letters 2005, 86, 143104.

(Continued)

*Primary Examiner* — Vongsavanh Sengdara
(74) *Attorney, Agent, or Firm* — Dority & Manning, P.A.

(57) ABSTRACT

Sensor are generally provided that include a layer of silicon oxide on a portion of a n+ layer to form an uneven surface where the layer of silicon oxide defines a thicker region than an exposed portion of the n+ layer. First and second metal contacts can be on the layer of silicon oxide, with first and second nanowires extending respectively from a first base on the first metal contact and a second base on the second metal contact. The first nanowire and the second nanowire are connected together at an apex to form a v-shaped nanocantilever, wherein the apex is positioned over the exposed n+ layer, and wherein the nanowires comprise indium and nitrogen. Methods of fabricating such sensors, along with methods of their use, are also generally provided.

18 Claims, 10 Drawing Sheets

(56) References Cited

OTHER PUBLICATIONS

Zaitsev, A. M. et al. "Carbon nanowire-based temperature sensor". Physics Status Solidi A 2007, 204, 3574-3579.

Cleland, A. N. et al. "A nanometer-scale mechanical electrometer". Nature 1998, 392, 160-162.

Rugar, D. et al. "Single spin detection by magnetic resonance force microscopy". Nature 2004, 430, 329-332.

Ekinki, K. L. et al. Nanoelectromechanical Systems. Review of Scientific Instruments 2005, 75, 061101.

Li, M. et al. "Bottom-up assembly of large-area nanowire resonator arrays". Nature Nanotechnology 2008, 3, 88-92.

Henry, T. et al. "Directed growth of horizontally aligned gallium nitride nanowires for nanoelectromechanical resonator arrays". Nano Letters 2007, 7, 3315-3319.

Cleland, A. N. et al. "Fabrication of high frequency nanometer scale mechanical resonators from bulk Si crystals". Applied Physics Letters 1996, 69, 2653-2655.

Li, M. et al. "Ultra-sensitive NEMS-based cantilevers for sensing, scanned probe and very high-frequency applications". Nature Nanotechnology 2007, 2, 114-120.

Hierold, C. et al. "Nano electromechanical sensors based on carbon nanotubes". Sensors and Actuators A 2007, 136, 51-61.

Mahboob, I. et al. "Intrinsic electron accumulation at Clean InN surfaces". Physical Review Letters 2004, 92, 036804.

Cai, Z. et al. "Synthesis and Properties of High-Quality InN Nanowires and Nanonetworks". Journal of Electronic Materials 2008, 37, 585-592.

Qazi, M. et al. "Two-dimensional signatures for molecular identification". Applied Physics Letters 2008, 92, 103120.

Huang, T. et al. "Gallium nitride Nanowire Nanodevices". Nano Letters 2002, 2, 101-104.

Khanal, D. R. et al. "Gate coupling and charge distribution in nanowire field effect transistors". Nano Letters 2007, 7, 2778-2783.

Cheng, G. et al. "Electronic properties of InN nanowires". Applied Physics Letters 2005, 87, 253103.

Chen, J. "Electrically excited infrared emission from InN nanowire transistors". Nano Letters 2007, 7, 2276-2280.

Chaudhry, A. et al. "Examining the anomalous electrical characteristics observed in InN nanowires". Journal of Nanoscience and Nanotechnology 2008, 8, 222-227.

Chang, C. et al. "Electrical transport properties of single GaN and InN nanowires". Journal of Electronic Materials 2006, 35, 738-743.

Timoshenko, S. P. et al. "Vibration Problems in Engineering" $4^{th}$ ed. 1974 (New York: Wiley) pp. 416-420.

Sader, J. "Parallel beam approximation for V-shaped atomic force microscope cantilevers". Review of Scientific Instruments 1995, 66, 4583-4587.

Koley, G. et al. "Gas sensing using electrostatic force potentiometry". Applied Physics Letters 2007, 90, 173105.

Sasaki, N. et al. "The relation between resonance curves and tip-surface interaction potential in noncontact atomic-force microscopy". Japanese Journal of Applied Physics 1998, 37, L533-L535.

Qazi, M. et al. "$NO_2$ detection by adsorption induced work function changes in $In_2O_3$ thin films". Applied Physics Letters 2007, 91, 043113.

Qazi, M. et al. "Trace gas sensing using nanostructure graphite layers". Applied Physics Letters 2007, 91, 233101.

Gudiksen, M. et al. "Synthetic control of the diameter and length of single crystal semiconductor nanowires". Journal of Physical Chemistry B 2001, 105, 4062-4064.

Hong, K. et al. "Diameter control of tungsten oxide nanowires as grown by thermal evaporation". Nanotechnology 2008, 19, 085604.

Ni, H. et al. "Young's modulus of ZnO nanobelts measured using atomic force microscopy and nanoindentation techniques". Nanotechnology 2006, 17, 3591-3597.

Park, I. et al. "Towards the silicon nanowire-based sensor for intracellular biochemical detection". Biosensors and Bioelectronics 2007, 22, 2065-2070.

Patolsky, F. et al. "Detection, stimulation, and inhibition of neuronal signals with high-density nanowire transistor arrays". Science 2006, 313, 1100-1104.

Tomchenko, A. A. et al. "Detection of chemical warfare agents using nanostructure metal oxide sensors". Sensors and Actuators B: Chemical 2005, 108, 41-55.

Zhang, J. " Growth and structural characterization of $InN/In_2O_3$ coaxial nanocables". Materials Letters 2006, 60, 2153-2157.

Cattanach, et al. "Flexible carbon nanotube sensors for nerve agent simulants". Nanotechnology 2006, 17, 4123-4128.

Pinnaduwage, L. A. et al. "Sensitive detection of plastic explosives with self-assembled monolayer-coated microcantilevers". Applied Physics Letters 2003, 83, 1471-1473.

Pinnaduwage, L. A. et al. "A sensitive, handheld vapor sensor based on microcantilevers". Review of Scientific Instruments 2004, 75, 4554-4557.

Pinnaduwage, L. A. et al. "Moore's law in homeland defense: an integrated sensor platform based on silicon microcantilevers". IEEE Sensors Journal 2005, 5, 774-785.

Zuo, G. et al. "Dual-SAM functionalization on integrated cantilevers for specific trace-explosive sensing and non-specific adsorption suppression". Nanotechnology 2007, 18, 255501.

Pinnaduwage, L. A. et al. "Explosives: A microsensor for trinitrotoluene vapour". Nature 2003, 425.

Pinnaduwage, L. A. et al. "Detection of trinitrotoluene via deflagration on a microcantilever". Journal of Applied Physics 2004, 95, 5871-5875.

Change, J. C. et al. "A modified microstamping technique enhances polylysine transfer and neuronal cell patterning". Biomaterials 2003, 24, 2863-2870.

Takii, Y. et al. "Microstamp-based micromachining for modulation of growth of cultured neuronal cells". JSME International Journal Series C 2004, 47, 956-961.

Taylor, A. M. et al. "Microfluidic multicompartment device for neuroscience research". Langmuir 2003, 19, 1551-1556.

Williams, S. R. et al. "Direct measurement of somatic voltage clamp errors in central neurons". Nature Neuroscience 2008, 11, 790-798.

Johnston, D. et al. "Interpretation of voltage-clamp measurements in hippocampal neurons". Journal of Neurophysiology 1983, 50, 464-486.

Spruston, N. et al. "Voltage- and space-clamp errors associated with measurement of electronically remote synaptic events". Journal of Neurophysiology 1993, 70, 781-802.

Aksenov, M. Y. et al. "Cocaine-medicated enhancement of Tat toxicity in rat hippocampal cell cultures: The role of oxidative stress and D1 dopamine receptor". Neurotoxicology 2006, 27, 217-228.

\* cited by examiner

INN NANOWIRE BASED MULTIFUNCTIONAL NANOCANTILEVER SENSORS

PRIORITY INFORMATION

The present application claims priority to U.S. Provisional Patent Application Ser. No. 61/384,432 titled "InN Nanowire Based Multifunctional Nanocantilever Sensors" filed on Sep. 20, 2010 of Goutam Koley, the disclosure of which is incorporated by reference herein.

GOVERNMENT SUPPORT CLAUSE

This invention was made with government support under ECCS-0846898 awarded by the National Science Foundation. The government has certain rights in the invention.

BACKGROUND OF INVENTION

Nanoscale sensors, in various forms, have been under intense research focus in the past several years due to their high sensitivity toward changes in many physical parameters such as mass, force, energy, stress, temperature, charge, and spin. Additionally, these systems promise high integration density and low power consumption, two of the most desirable aspects of an integrated system. A combination of all these properties can lead to potential applications of these sensors in a large variety of civilian and military applications. There are currently two approaches for nanoscale sensor fabrication: (1) top-down and (2) bottom-up. In the top-down approach, expensive and complicated fabrication processes are utilized to realize the nanostructures, which limits their applications to only very specific and niche areas. In the bottom-up approach, the nanostructures are realized through inexpensive nanowire (NW) synthesis processes that can open up opportunities for widespread applications. In addition, the uniformity and quality of the nanostructures (which seriously impact the device characteristics) that are naturally obtained during the synthesis process cannot be achieved by current state-of-the-art nanofabrication tools. However, controlled positioning of the nanowires over a large area has been quite difficult to achieve so far, restricting their applications to individual devices, or to low levels of integration.

Nanoelectromechanical systems (NEMS) constitute a very important branch of nanoscale sensors where the system stimulation and transduction is performed by electrical means, but the actual sensing is performed mechanically, taking advantage of the exceptionally high quality factors (in resonance) available in these systems that are normally not possible to achieve in electrical systems. There have been attempts to fabricate NEMS devices based on nanowires and nanotubes (NTs). However, in addition to the problem of integration as mentioned above, NEMS sensors in general, and those based on nanowires (or nanotubes) in particular, suffer from the problems of transduction of the mechanical signal into electrical form. Various techniques have been employed to transduce the mechanical deflection of the NEMS device, which includes optical, electron beam, magnetic, radio-frequency transmittance, and piezoresistive. However, with the exception of piezoresistive transduction, none of these techniques are applicable for simultaneous deflection transduction of multiple NEMS devices in an integrated circuit. Another significant limitation with most NEMS sensors reported in the literature is they almost invariably have a linear geometry (due to obvious ease in fabrication and alignment), and are fixed at both ends, acting as a beam resonator rather than a cantilever resonator. This geometry greatly reduces the sensitivity of these devices to changes in physical quantities that needs to be measured.

Other major characteristics of nanoscale sensors are strongly influenced by the properties of the material (usually semiconductor) from which it is made. Usually, for chemFET type sensing (based on surface depletion caused by adsorbed molecules) the material should have a high carrier density, high mobility, chemical inertness, and thermal stability. NEMS devices would additionally require smooth and highly crystalline nanowires for high quality factor, and large piezoresistivity for efficient transduction of device deflection. Most semiconductors and their nanowires display some of the above mentioned properties, but rarely all.

Thus, a need exists for an improved geometry and material construction of the semiconductor material for the cantilever used as the sensor to improve detection sensitivity and signal transduction.

SUMMARY

Objects and advantages of the invention will be set forth in part in the following description, or may be obvious from the description, or may be learned through practice of the invention.

Sensors are generally provided that can include, according to one particular embodiment, an n+ layer and a layer of silicon oxide on a portion of the n+ layer to form an uneven surface where the layer of silicon oxide defines a thicker region than an exposed portion of the n+ layer. A first metal contact can be on the layer of silicon oxide, and a second metal contact can be on the layer of silicon oxide. A v-shaped nanowire is also included in the sensor. The v-shaped nanowire defines a first arm and a second arm extending respectively from a first base contacting the first metal contact and a second base contacting the second metal contact. The first arm extents over the exposed n+ layer for a first length, and the second arm extents over the exposed n+ layer for a second length. The first arm and the second arm are connected together at an apex to form the v-shaped nanocantilever, wherein the apex is positioned over the exposed n+ layer, and wherein the v-shaped nanowire comprises indium and nitrogen (e.g., InN).

In certain embodiments, the first arm and the second arm can have an average diameter of about 10 nm to about 50 nm (e.g., about 20 nm to about 40 nm), independent of each other. In one particular embodiment, the first length and the second length can be substantially equal, though in other embodiments they may be substantially different.

In one particular embodiment, the first arm and the second arm can be connected together at the apex at an angle of about 30° to about 75° (e.g., about 35° to about 60°).

The sensor can, in certain embodiments, further include a substrate, wherein the n+ layer is positioned on the substrate. For example, the substrate can be a p-type substrate (e.g., a p-type Si substrate).

In one particular embodiment, the n+ layer can defines a functionalized surface over the exposed portion. For example, the functionalized surface can be configured to bind to an analyte (e.g., a virus, a protein, DNA, RNA, a volatile organic species, etc.).

The v-shaped nanowire can, in particular embodiments, comprise a shell layer positioned around a core layer. For example, the shell layer can comprise $In_2O_3$, and/or the core layer can comprise InN.

Methods of fabricating such sensors, along with methods of their use, are also generally provided.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION

Figure 1A:
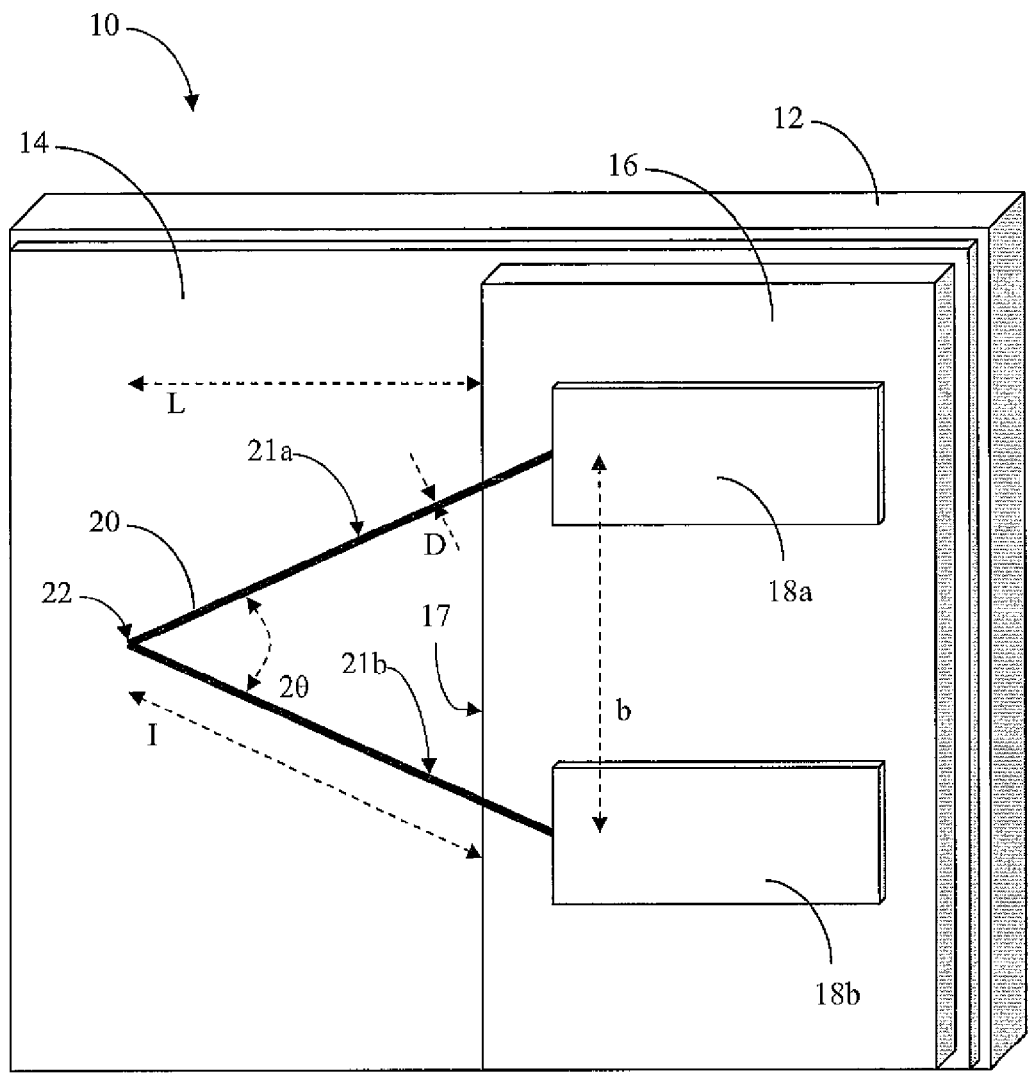
FIGS. 1A and 1B show exemplary v-shaped nanocantilever sensors according to certain embodiments of the present invention.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale (e.g., from about 1 nm to about 999 nm). For example, wires having an average diameter on the nanometer scale (e.g., from about 1 nm to about 999 nm) are referred to as "nanowires". Wires having an average diameter of greater than 1,000 nm (i.e., 1 μm) are generally referred to as "microwires", since the micrometer scale generally involves those materials having an average size of greater than 1 μm.

Generally speaking, the design, fabrication, and use of indium-nitrogen (InN) nanowire (NW) based multifunctional V-shaped nanocantilever (VNC) sensors are disclosed for the detection of analyte molecules in ambient conditions and investigation of electrical signal propagation in neurons. In particular, the development of v-shaped nanocantilever (VNC) sensors utilizing the special properties of indium-nitrogen (InN) nanowires is generally described herein.

The special shape and geometry of the nanowires, which can be achieved inexpensively through barrier patterning, allows not only for their use as true cantilever resonators, but also to transduce their deflection from change in resistance between the two arms (caused by deflection in an electric field as well as possible piezoresistive effects). For example, a V-shaped nanocantilever can not only dramatically improve detection sensitivity, but can also provide ready means for signal transduction (based on resistance change caused by deflection) through contacts established at the two arms.

The v-shaped nanocantilevers can be utilized for highly sensitive measurements/detections of surface work function (SWF, $\phi$), electric potential (V), conductance ($\sigma$), and surface stress (S) changes. Of these, SWF will be sensed using a resonant v-shaped nanocantilever, while stress, conductance and electric potential (in neurons) changes will be sensed in the static mode. The deflection of the v-shaped nanocantilever in either static or dynamic mode can be transduced from the change in its surface depletion depth, and hence in the nanowire resistance, as it moves in a strong electric field. This method of deflection transduction is only possible in a nanowire with a small diameter (e.g., average diameter of about 10 nm to about 50 nm, such as about 20 nm to about 40 nm) where the change in carrier concentration due to nm level deflection (causing changes in the thickness of the air dielectric between the VNC and the reference electrode as in FIG. 1) can be quite significant (>0.1%).

Figure 1B:
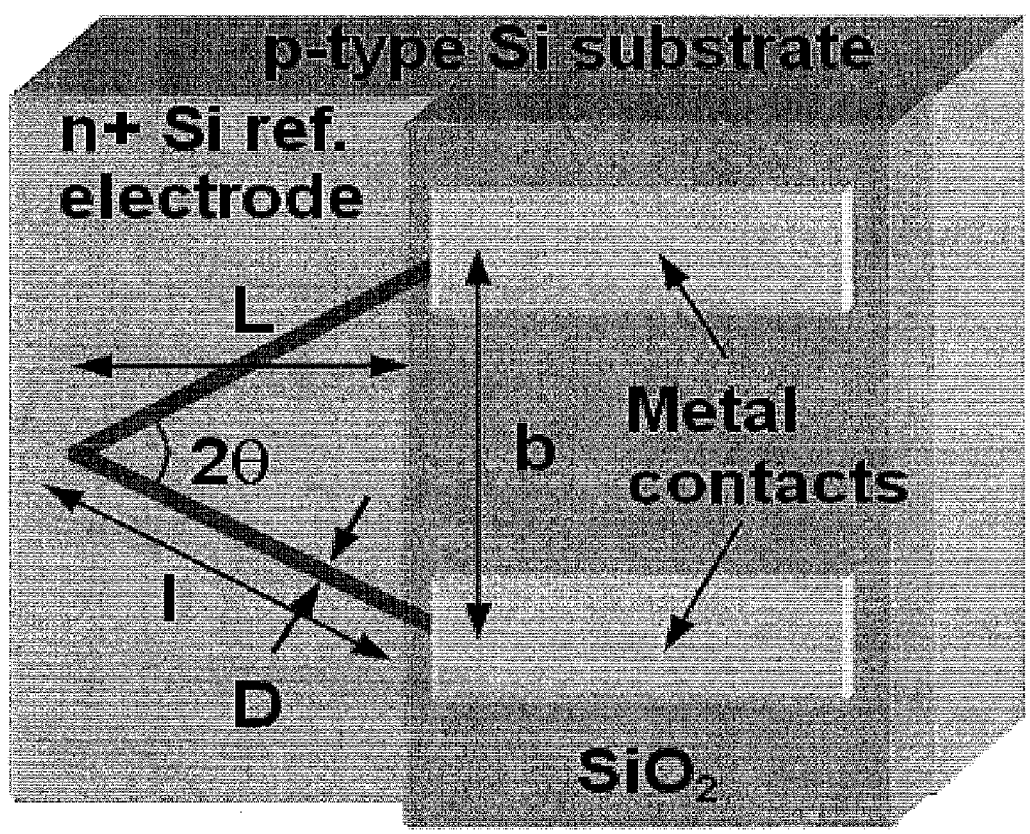

FIG. 1A shows an exemplary v-shaped nanocantilever device 10 according to one embodiment of the present invention. The v-shaped nanocantilever device 10 includes a substrate 12. The substrate 12 can be, in one particular embodiment, a p-type substrate, such as a p-type Si substrate as shown in FIG. 1B. An n+ layer 14 is on the substrate 12, such as the n+ Si ref. electrode shown in FIG. 1B. A layer 16 of silicon oxide ($SiO_2$) is shown on the n+ layer 14, while leaving a portion of the n+ layer 14 exposed. Thus, an uneven surface is formed where the layer 16 defines a thicker region than the areas where the n+ layer 14 is exposed.

Metal contacts 18a, 18b are formed on the layer 16. Extending from the metal contacts is a v-shaped nanocantilever 20, where the base of each arm 21a, 21b contacts the metal contact 18a, 18b, respectively. The arms 21a, 21b connect to each other at the apex 22 to form the v-shape having an angle "2θ". The base of each arm 21a, 21b is spaced apart from each other at a base distance "b". Each arm 21a, 21b have an arm length "l" extending over the exposed n+ layer 14 (i.e., from the edge 17 of the layer 16 to the apex 22), and a diameter "d". The length "L" is measured from the apex 22 to the edge 17 of the layer 16 to the apex 22.

These parameters can be adjusted to conform the nanocantilever device 10 to a particular use. However, in certain embodiments, the nanocatilever 10 can be formed where: 2θ is about 30° to about 75° (e.g., about 45° to about 60°); b is about 1 μm to about 5 μm (e.g., about 2 μm to about 3 μm); l is about 2 μm to about 5 μm (e.g., about 3 μm to about 4 μm);

d is about 10 nm to about 50 nm (e.g., about 15 nm to about 20 nm); and L is 1 µm to about 5 µm (e.g., about 2 µm to about 3 µm).

The nanocantilever 20 can generally be constructed from indium nitrogen (InN) nanowires, which generally exhibit high carrier density, high mobility, chemical inertness, and thermal stability. Additionally, InN nanowires can have a high density of carriers present in the nanowire (from unintentional doping), a large fraction of which is can be on the surface. Second, InN nanowires can exhibit spontaneous and barrier induced growth redirections while otherwise growing straight on the substrate surface. The first property, when combined with high mobility of these nanowires (results indicate mobility>1000 $cm^2$/Vs is possible), can lead to highly sensitive deflection transduction (based on surface depletion change) as will be utilized in our NEMS devices. The second property has been recently observed, and can be exploited to synthesize nanowires of special shapes and sizes by controlling their growth directions using patterned barriers.

The small diameter attainable for these InN nanowires, along with the high density and mobility of the carriers, allows them to be densely packed in a small area for use in multimodal detection of analytes based on measured changes in multiple parameters (e.g., SWF, mass, electrical conductivity, etc.) due to molecular attachment. Multimodal detection is advantageous since common functionalization layers generally do not offer high enough analyte selectivity that is often required for detection in critical situations like explosives in battlefield or in airport security. The multimodal detection technique is also capable of unique identification of a single analyte by determining its multi-dimensional signature. The v-shaped nanocantilevers can also be utilized as nanoscale heaters (with much lower power dissipation compared to the microscale ones), offering another approach to differentiate between analyte molecules, based on their selective desorption at different temperatures. The natural triangular geometry of the v-shaped nanocantilevers combined with their favorable electrical properties makes them very suitable for detection of electrical signal propagation in neuronal cells with very high spatial and temporal resolution, which is currently unavailable. The combined effects of high sensitivity of these sensors, nanoscale size, very low power consumption, and inexpensive synthesis process, can have far-reaching and transformative impacts in the fields of defense, homeland security, environmental monitoring, drug discovery, and neuro-medicine.

The methods disclosed herein provide for the development of a viable and inexpensive fabrication approach for NEMS sensors, instead of the presently relied upon expensive methods of electron-beam or ion-beam lithography. In one embodiment, growth of InN nanowires can be performed using an improved CVD furnace with three-zone temperature control (Lindberg Blue). This furnace can provide more accurate control of the temperature profile, and more uniform distribution of the reactant specie than is currently possible using a single temperature zone furnace. Thus, better diameter control and growth uniformity of the nanowires can be achieved. The NWs can be grown using Au catalyst patterns on $SiO_2$/Si substrates as in our preliminary experiments. Also, "holey" $SiN_x$ film can be utilized for growth thereon, which will allow quick and direct TEM analysis of the as-grown nanowires without transfer to a separate Cu grid by sonication. The growth parameters can control the three primary aspects of the NWs: (i) diameter, (ii) bending angle on reaching a barrier, and (iii) growth along the edge of a barrier. The properties of the VNC can depend critically on the diameter of the nanowire. Control of the nanowire diameter formed can be achieved through control of the size of the catalyst particle(s) (i.e., catalyst spot size and thickness), flow rate of the gaseous precursors (e.g., $NH_3$, and $N_2$ containing In vapor), growth temperature, and growth pressure, in addition to other growth parameters.

The bending angle of the nanowires can depend on whether the growth direction is changed between equivalent [110] directions (producing 60° and 120° bends), or between [110] and [1$\bar{1}$0] directions (producing 30° and 90° bends). The flow rate of the precursors, the growth temperature and pressure can be adjusted to affect the bending angle of the nanowire when it is obstructed by a barrier. Hence, a systematic variation of these parameters can be made during nanowire growth to control the nanowire diameter and the bending angle.

The growth of the nanowire along the barrier is a special condition, where the NW growth is no longer free, but is controlled by the adhesion force between the nanowire and the barrier edge, which can be controlled by growth rate and growth temperature.

Since the growth directions of the nanowires can be changed by the presence of obstacles, lithographically patterned $SiO_2$ barriers can be used to fabricate the V-shaped nanowires. Two different strategies can be utilized to control the growth directions of the nanowires: (a) utilization of patterned barriers as shown in FIG. 7A, which can redirect the growth of the nanowires backwards at specific angles to result in V-shaped nanowires with a specific apex angle and (b) utilization of patterned barrier as shown in FIG. 2B, which will guide the nanowire growth along its contour resulting in the desired shape and bending angle. While the former approach is lithographically simpler, it does not have the versatility of the later approach where the V-shaped nanowires can be given virtually any shape and bend angle depending on the lithographic patterns. The later approach can also be more controllable and better suited for production of VNC arrays. For applications of the VNCs as sensors in certain embodiments, S can be about 4 µm, so that a vertical height L of the final VNCs can be about 2 µm, after etching and release from the $SiO_2$ layer. The vertical angle 2θ can be about 60° in certain embodiments.

Figure 2A:
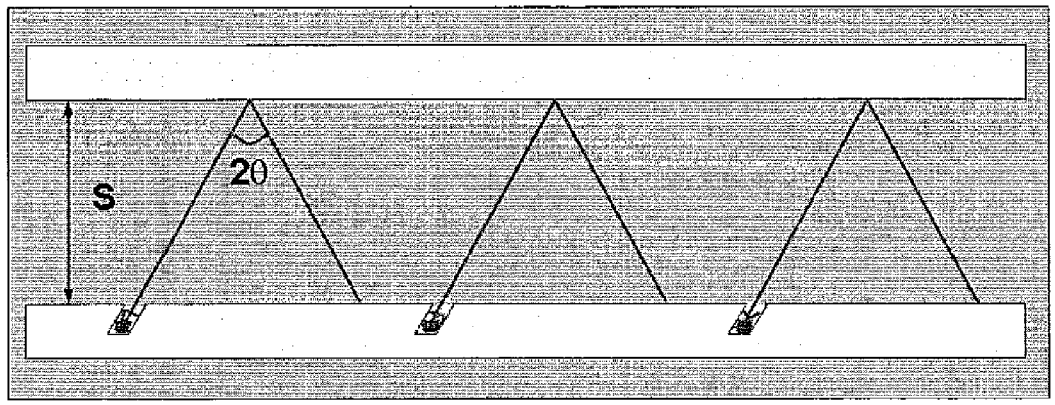
FIG. 2 shows an exemplary nanowire array grown by (2A) directed growth and bending angle control and (2B) using patterned barriers as growth templates.
Figure 2B:
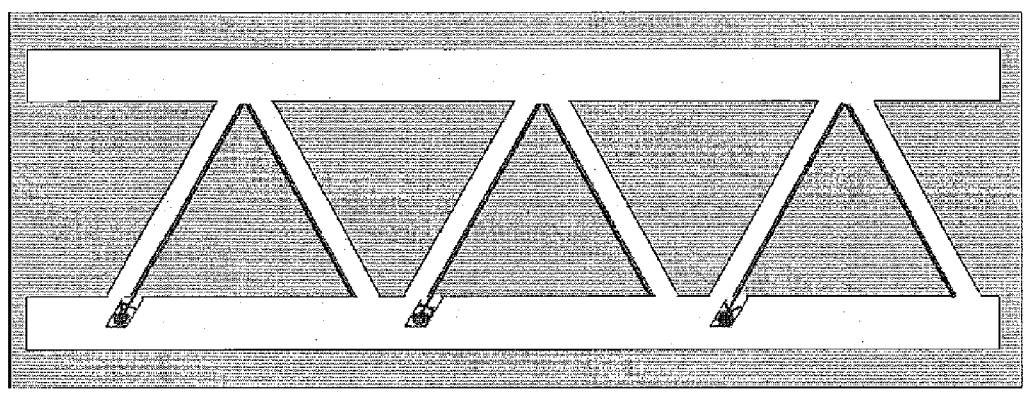
Figure 3A:
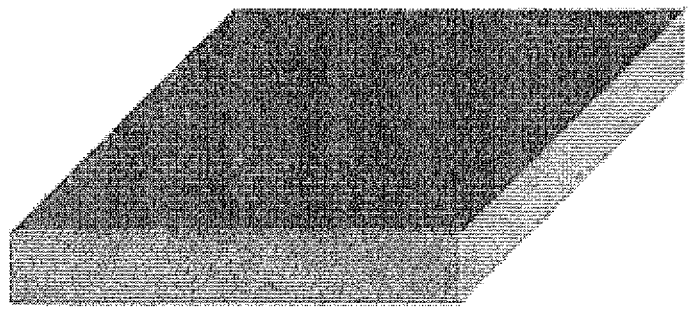
FIG. 3 sequentially shows an exemplary method of fabricating the v-shaped nanocantilever sensor starting with (3A) a p-type Si wafer, (3B) forming a n+ ion implantation in different regions on the p-type Si wafer, (3C) depositing functionalization layers, through multiple iterative steps (if necessary), (3D) depositing high quality $SiO_2$, (3E) depositing metal contacts onto the functionalization layers, (3F) forming $SiO_2$ barrier patterns and V-shaped nanowire growth, (3G) metallization of contacts for the nanowires, and (3H) etching the $SiO_2$ to release the nanowires and expose the functionalization layers.
Figure 3B:
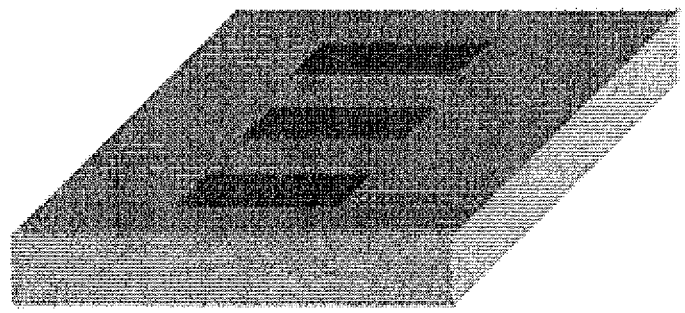
Figure 3C:
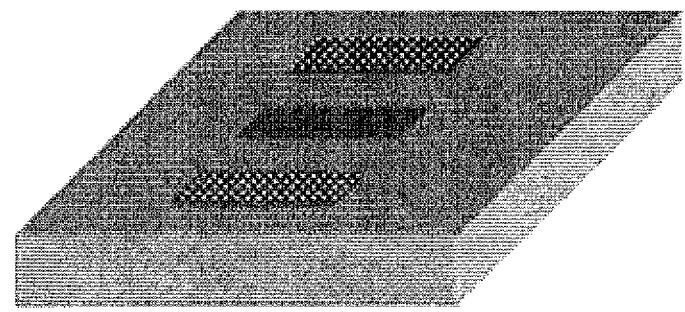
Figure 3D:
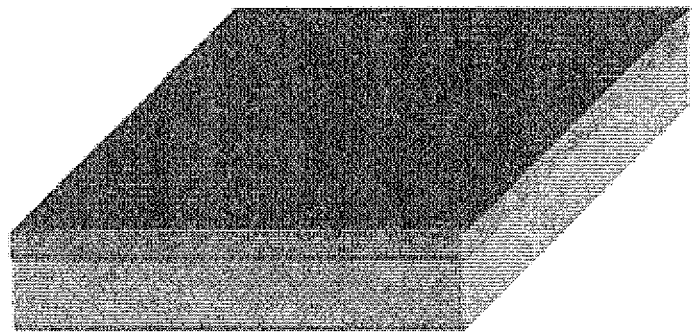
Figure 3E:
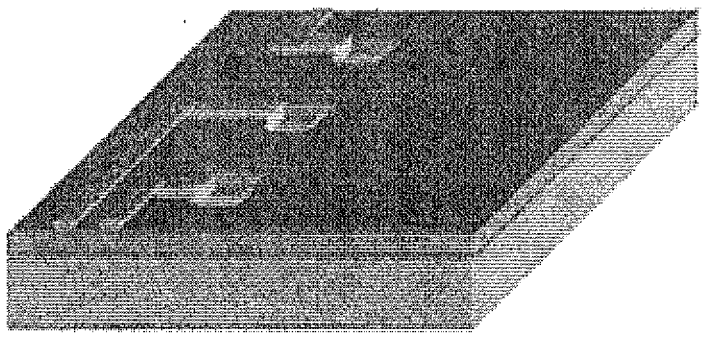
Figure 3F:
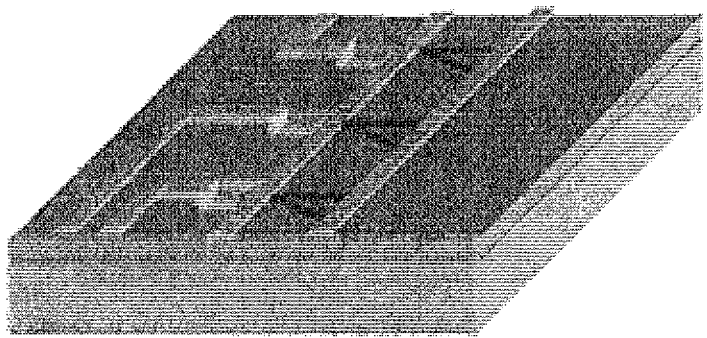
Figure 3G:
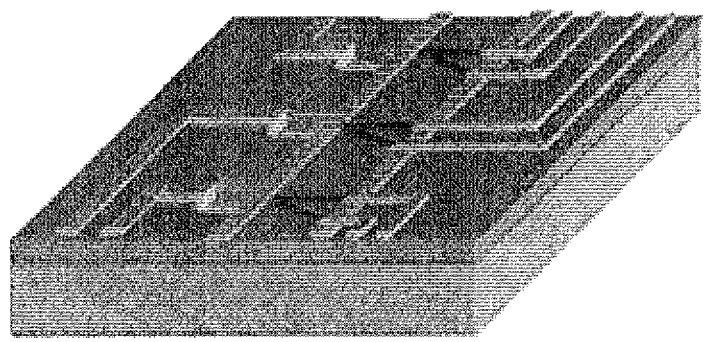
Figure 3H:
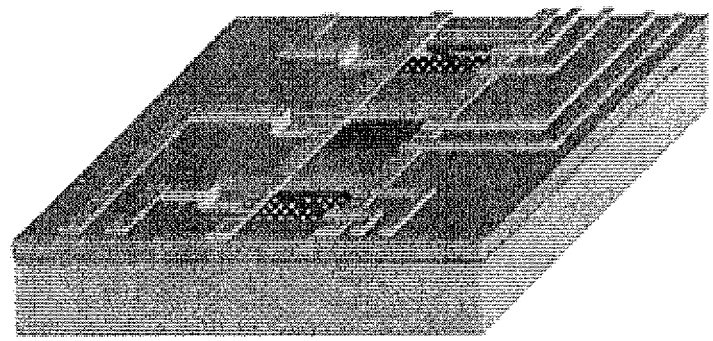

The VNCs can be fabricated from the V-shaped NWs synthesized by CVD on $SiO_2$/Si substrates using patterned $SiO_2$ barriers (see FIG. 2). Exemplary lithographic steps for fabrication of the InN nanowires are as shown in FIG. 3.

In particular FIG. 3A-3H sequentially show an exemplary fabrication method for v-shaped nanocantilevers. Fabrication steps for the VNC sensor are shown in FIGS. 3A through 3H. (a) p-type Si wafer (b) n+ ion implantation in different regions (c) deposition of functionalization layers, through multiple iterative steps, if necessary (d) high quality $SiO_2$ deposition (e) deposition of metal contacts to the functionalization layers (f) $SiO_2$ barrier patterning and V-shaped nanowire growth (g) contact metallization for the nanowires (h) $SiO_2$ etch to release nanowires and expose functionalization layers.

The metal oxide functionalization layers can be deposited by plasma enhanced CVD, while metals (Pd, Pt, or Au) can be deposited using thermal or e-beam deposition in vacuum. The final release of the nanowires can be performed by controlled buffered oxide etch (BOE) of the $SiO_2$ layer under the V-shaped InN NW (InN is not attacked by BOE).

Figure 4:
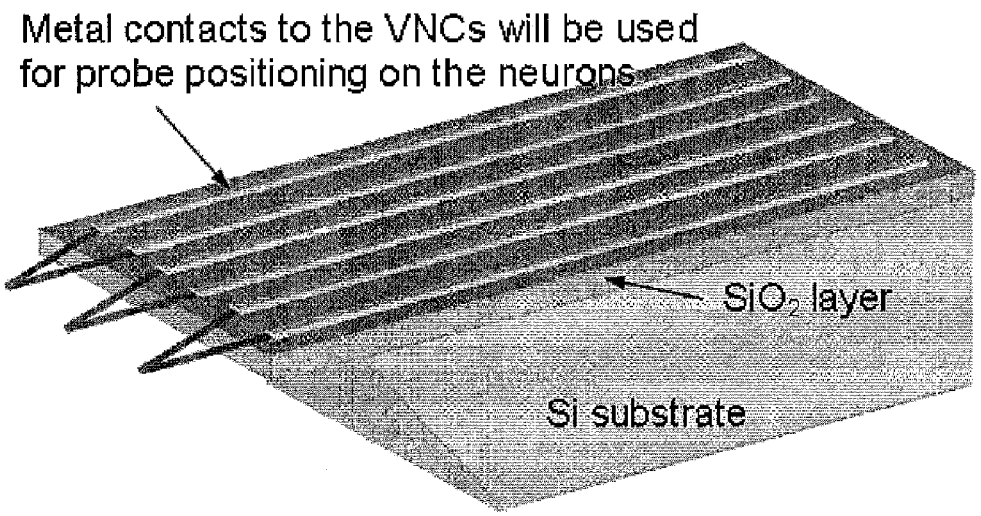
FIG. 4 shows v-shaped nanocantilever probe arrays for electric potential measurements in neurons.

For electrical signals measurements in neurons, special VNC probes protrude out from the edge of the $SiO_2$ layer on top of a Si base chip as shown in FIG. 4 can be fabricated. For fabrication of these arrays, deep reactive ion etching of Si from backside using inductively coupled plasma can be performed, after the growth of the nanowires on $SiO_2$ (e.g., 4 µm)/Si substrate. Then, the NWs can be released from the front side by BOE etching of $SiO_2$. This can allow a part of the $SiO_2$ layer to project out from top of the Si substrate (see FIG. 4), which can help in placing the probes. The probes can be electrically isolated from the surroundings by using 1 μm thick parylene or $SiN_x$ coating.

In certain embodiments, the VNCs themselves can be insulated with a thin (e.g., about 3 nm to about 5 nm) layer of $SiO_2$ to prevent leakage of current from the VNC.

As stated, the InN VNC sensors are capable of performing highly sensitive detection based on changes in 3 different physical parameters: SWF ($\Delta\phi$), conductivity ($\Delta\sigma$), and surface stress ($\Delta S$). Of these, detection based on $\Delta\phi$ is the most versatile and widely applicable, where various types of analyte molecules can be sensed by simply changing the functionalization layer on the substrate during fabrication. For detection based on $\Delta S$, the VNC, just like a microcantilever, can be coated on one side with appropriate selective layers, which requires more functionalization steps. $\Delta\sigma$ based detection also requires the presence of selective layers on the VNC, and the overall change in conductivity can be measured for detection. The choice of either of these modes, either individually, or in combination (for multimodal detection), depends on the properties of the functionalization layer corresponding to a target analyte, although, sensing based on $\Delta\phi$ measurements can always be utilized unless the functionalization layer is a solid with low melting point (such as a polymer). Even then, a thin layer of the selective film can be deposited on the VNC post-fabrication, if the coating does not significantly alter the resonance characteristics of the VNC. The other two modes depend on modifying the VNC specifically, which however, does not pose a significant problem (except when a highly conducting material needs to be deposited), since they detect in the static mode. However, simultaneous measurements of any two of these parameters (for multimodal detection), using the same functionalization layer, can be more restrictive. Change in conductivity, either due to surface depletion caused by direct molecular adsorption, or due to bending induced depletion caused by electric field (former related to $\Delta\sigma$, and the later to $\Delta S$) can be measured using a dc picoamperemeter.

Figure 5:
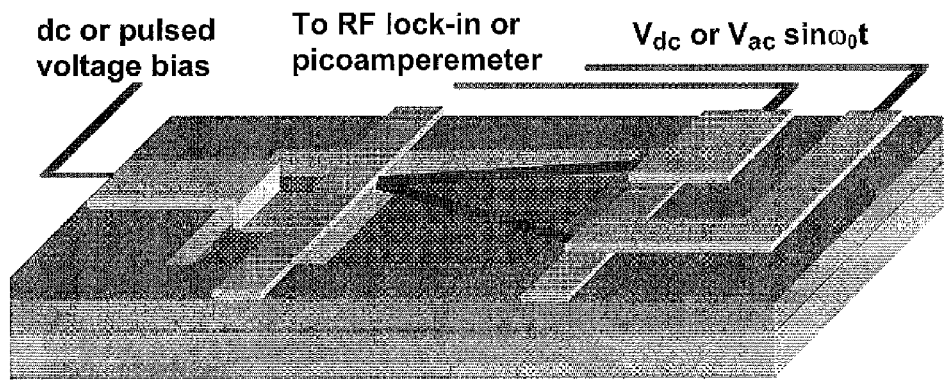
FIG. 5 shows a sensing configuration for an exemplary v-shaped nanocantilever sensor.

A single VNC sensor with the relevant electrical connections is shown in FIG. 5. The dc bias to the substrate can be used to compensate for the natural difference in SWF between the probe and the functionalization layer, as well as, to create depletion in VNCs due to bending in static sensing modes. The pulsed bias can be used for VNC calibration.

The sensors can be calibrated by performing detection based on $\Delta\phi$ measurements using trace $H_2$ (with $N_2$ carrier) as the test analyte, and Pt or Pd films as the functionalization layers (to be deposited in the fabrication steps). For measurement of single molecule sensitivity, 10 ppb $H_2$ (diluted in $N_2$) can be utilized as the test gas, and injected into the test chamber (~100 $cm^3$) at a slow rate of 1 sccm/min for one second duration in each shot. A Pt (or Pd) metal film of (e.g., having a size of about 1 $mm^2$) can be deposited on the $SiO_2$/Si chip during fabrication for the injected hydrogen to adsorb on. Assuming that most of the hydrogen will be adsorbed, about 0.33 atomic fraction can be adsorbed on an average on the overlap area of the VNC (e.g., $4\times20\times10^{-3}$ $\mu m^2$). Thus, in approximately 3 shots, a molecule of $H_2$ would adsorb on Pt in the overlap area, and a step change in the amplitude of the VNC sensor could be observed after 3 shots, on an average. Each hydrogen molecule adsorbed in the sensor overlap can produce an average SWF change of ~0.1 mV, which will be possible to detect using the VNC sensor. Following sensor calibration through trace $H_2$ detection experiments, trace amounts of chemical warfare agents (CWAs) DCP and DMMP (which are sulfur mustard gas, and nerve gas Soman simulants, respectively), and explosives PETN and TNT, can be detected in vapor form.

Detection of CWAs can be performed using an $In_2O_3$ functionalization layer, which has very high responsivity to DCP and DIMP. The selection of $In_2O_3$ for detection is advantageous since it is fairly easy to grow an $In_2O_3$ shell layer on InN VNCs by thermal oxidation in $O_2$/Ar mixture. Since the VNCs can be used as nanoheaters by passing appropriate current through them, the oxidation can be performed quite easily and selectively after they are fully fabricated. Thermally grown $In_2O_3$ functionalization layer also allows all three sensing modes to be utilized enabling unique identification of analytes, although for $\Delta S$ based detection, one side of the VNC needs to be covered with a thin $SiO_2$ layer to create asymmetric stress due to molecular attachment.

Although detection of CWAs is possible at room temperature, best sensitivity may be obtained at higher temperatures (e.g., about 300 to about 400° C.), Fortunately, all the detection modes require passing current through the VNC for transduction, and the level of current used in each mode can be adjusted to achieve the required temperature of the nanowire. Of course, the VNCs will have to be calibrated for the ac or dc current required for attaining a particular temperature. Normally, large area microcantilever sensors need to be heated by expending several mWs of power to get heated to several hundred degrees. However, VNCs can be heated with a few tens of μW power (e.g., about 10 μW to about 50 μW), a part of which is dissipated to transduce their deflection or conductance change.

For the tri-modal detection to be used for the detection of CWAs, three separate VNCs can be used, so that simultaneous measurement of $\Delta\phi$, $\Delta\sigma$, and $\Delta S$ transients is possible. Unique signature gradients $S_{G1}=\Delta\phi/\Delta\sigma$, and $S_{G2}=\Delta\phi/\Delta S$ can be obtained from the measurements, which can then be used to determine the coordinates of DCP and DMMP in a 2-dimensional map. The co-ordinates for common interfering molecules such as, Hexane, Xylene (simulants for gasoline and diesel fuel, respectively, which are common interferents), water vapor, $NH_3$, and $NO_x$ can also be determined for comparison. If needed, $S_{G1}$ and $S_{G2}$ can be obtained at different temperature to aid in the unique identification of DCP and DMMP among the other interferents.

Detection of explosives (e.g., TNT and PETN) can be performed using mercaptobenzoic acid (MBA) and mercaptonicotinic acid (MNA) self assembled monolayers (SAMs) to functionalize the adsorption surface to advantage of the strong interaction between —COOH and —$NO_2$ groups. For example, a bi-modal detection scheme based on $\Delta\phi$ and $\Delta S$ measurements can be utilized, and unique signature $S_{G2}=\Delta\phi/\Delta S$ of the analytes can be determined. For $\Delta\phi$ measurement, a Au/Cr film can be deposited during fabrication process, which will be functionalized later with the SAM layer, by simply putting a drop of MBA or MNA on the particular VNC pit. For functionalizing the VNC for measurement of $\Delta S$, a thin (e.g., about 3 nm to about 5 nm) insulating layer of $SiO_2$ can be deposited on the VNC followed by a thin layer (e.g., about 5 nm) of Au, which can finally be functionalized using the MBA or MNA SAM. Obviously, the thickness of the VNC may increase, making it somewhat less sensitive to $\Delta S$. To compensate for this, the length of the VNCs can be increased during growth process as appropriate.

Similar to CWA sensing, the $S_2$ signatures of other —$NO_2$ containing analytes (e.g., DNT, nitro-toluene, and nitro-benzene) can be found and used for unique identification of TNT or PETN vapors. The explosive vapor for testing can be generated by first isolating the STB chamber after filling it with air, and then producing a calibrated vapor pressure by controlling the temperature (above or below 300 K) of the container housing the explosive powder, which will be placed inside the STB chamber in close proximity to the VNC sensors arrays.

Using the VNCs as nanoheaters, TNT vapor can be detected by an interesting technique of deflagration, where vapor of TNT condensed on a cantilever can be exploded by heating at a temperature of about 500° C. to release a high amount of thermal energy that can be sensed by the cantilever itself. Since the sensitivity depends on the area of the cantilever that is used for sensing, the detection sensitivity can be far superior to those demonstrated using microcantilevers (typical dimensions $10^{-4}$ cm$^{-2}$), where ~50 pg sensitivity for TNT was obtained. For this experiment, TNT vapor can be allowed to accumulate on the surface of a VNC sensor by keeping the heated TNT source close to the VNC sensor for a few minutes, and then a pulse of high current can be pulsed through the VNC, enough to raise the temperature to about 500° C. (as determined from the calibration performed for CWA sensing), resulting in explosion of the TNT that raises the temperature of the VNC sensor abruptly for a short duration (until all the TNT burns off), which can appear as a sudden reduction in current (due to change in resistance) or as a "bump".

For measurements in neurons, a specially fabricated VNC probe arrays can be used configured to withstand exposure to the neuron bath solution. The VNC array based measurements offer much more versatility in the measurements of cell potential compared to Si NW FET based measurements, which have probes only at fixed locations. In addition, the presence of electrons at the surface of the InN nanowires, and their high mobility can lead to much higher sensitivity in the measurement of electrical signals. Measurements of the action potential propagation in a single neuron (from fetal rat hippocampus) can be made by positioning the array of VNC probes at multiple locations on the axon as shown schematically in FIG. 6A. For this, the axon needs to grow in a reasonably straight line, which can be achieved by polylysine patterning. The square regions of about 50 μm sides, which can promote cell body adhesion, and further define about 2 μm wide lines that can help define subsequent axon growth. The patterning can be done by commonly used PDMS stamping based on a soft lithography procedure. Initially, the cell suspensions can be transferred to patterned chips for 1 hour for adhesion, and then the excess cells outside patterned regions can be washed out. Incubation (e.g., for at least a week) can allow for directed neuronal growth. For the measurement of action potential characteristics propagating in the axon, probe 1 positioned at the soma (cell body) can be used for stimulation by applying square voltage pulses of 0.5 ms duration, whose magnitude can be varied from ±0.1 V to ±1 V dc. The other probes can be used to measure the signal (manifested as change in conductance of the probes), and simultaneous recording will be performed to determine the propagation speed, signal magnitude and temporal spreading of the action potential. Similar measurements can also be performed on the dendrites to determine the action potential propagation characteristics and compared with those through the axon. The action potential propagation is blocked in the presence of a neurotoxin.

Figure 6A:
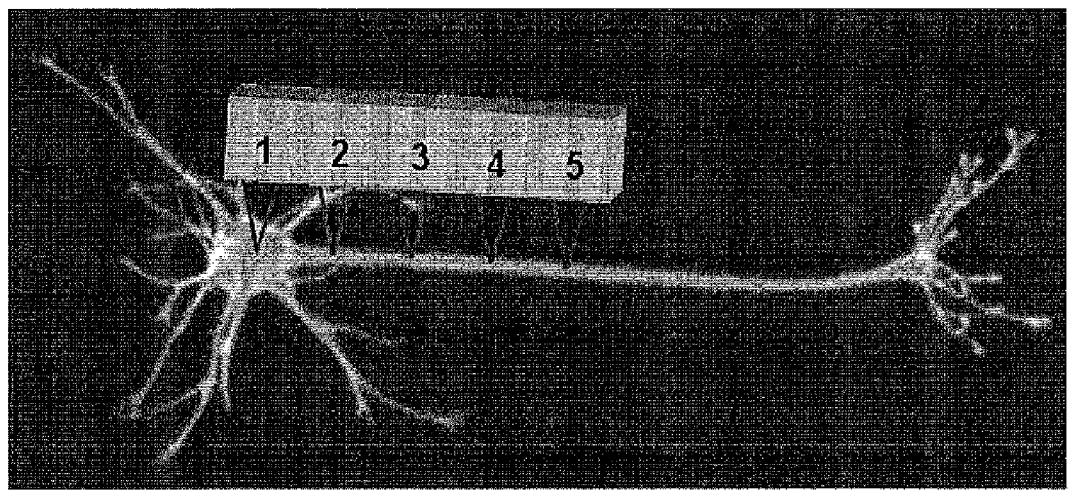
FIG. 6 shows an exemplary schematic diagram showing pre- and post-synaptic neurons and probe positions.
Figure 6B:
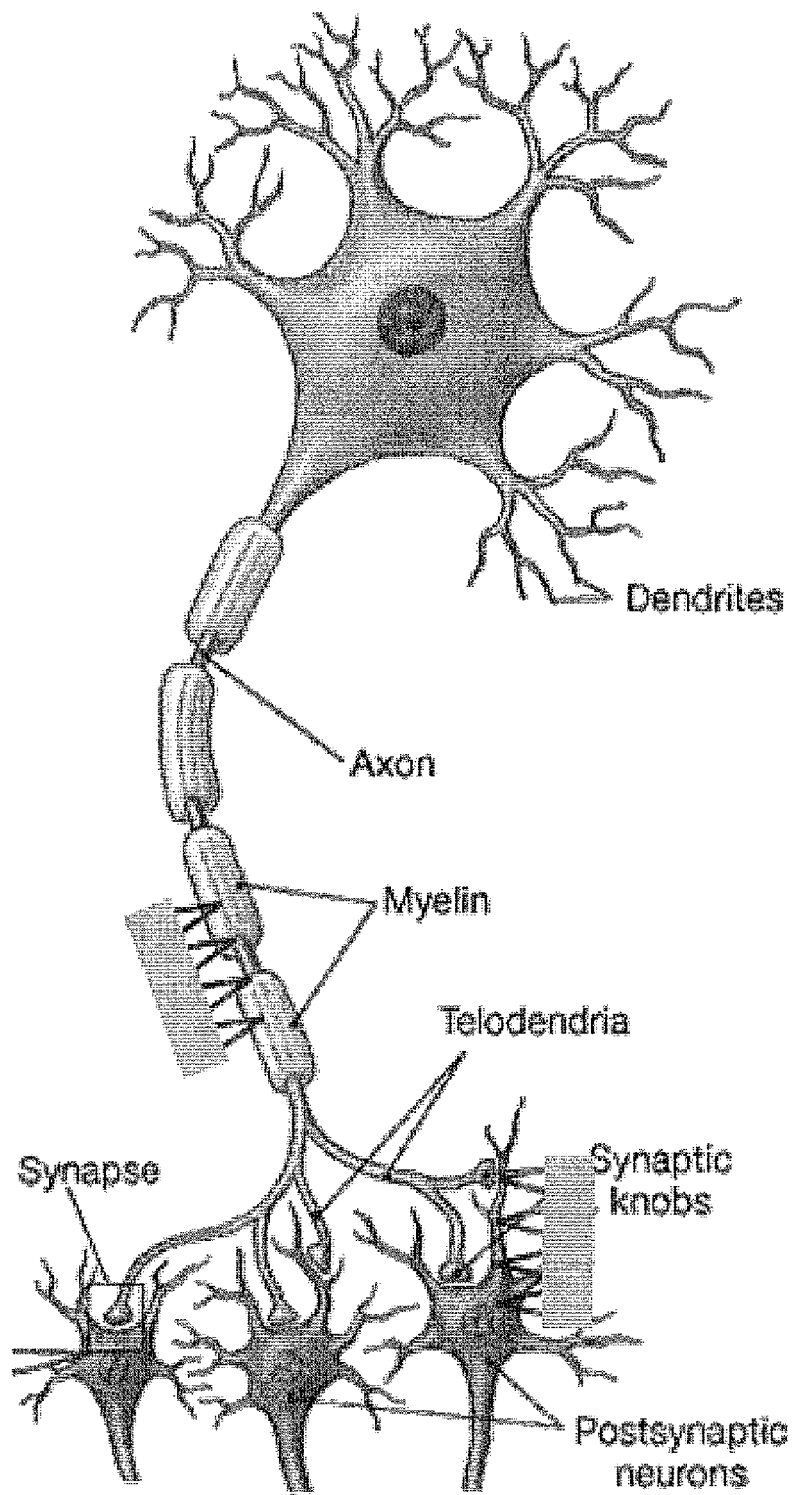

The somatic voltage clamp technique, used for over about three decades for characterization of synaptic physiology, cannot accurately measure the amplitude and time course of dendritic synaptic conductance. The dendrite, which acts like an electrical filter, continuously attenuates the signal flowing through it, and spreads it temporally, before it reaches the soma. This is unlike the signal propagation in axon, where the signal propagates with very little attenuation and spread, and at a higher speed. Thus, measurement of the signal conduction in the dendrite of a postsynaptic neuron using an array of VNC probes can provide very important information regarding the attenuation, synaptic speed and time delay, which are normally not possible to obtain using microscale voltage clamps. The utilization of two interacting neurons, as shown in FIG. 6B, can be used to study the signal propagation characteristics. An array of probes can be positioned near the end of the axon of the pre-synaptic neurons and another array on the dendrite of the post-synaptic neuron. The signal characteristics in the dendrite can be compared with that obtained earlier from a single cell to isolate the effects of the synapse on signal propagation in a postsynaptic neuron.

The electrical characteristics of neurons are significantly affected in the presence of toxic chemicals, i.e. drugs, and viral proteins that are manifested in outward physiological behavioral modification of animals and humans. The VNC probe arrays present a very attractive and unique opportunity for studying the effects of toxic materials on electrical pathways in neurons. For measurements, two probe arrays can be positioned on a set of pre- and postsynaptic neurons as shown in FIG. 6, with protein added to the physiological bath solution. The temporal variation of the electrical characteristics (speed, attenuation, and time spread of the action potential) can be found for both the presynaptic neuron and the postsynaptic dendrite.

The transduction method disclosed herein is based on deflection induced gating of the v-shaped nanocantilever sensor (in gateless transistor configuration), offering an innovative solution that addresses the critical issues of scalability and large scale integration in MEMS based integrated circuits. The multimodal detection technique to be developed in this project utilizing multiple parameter sensing capability incorporated in an array of nanoscale devices can significantly enhance the reliability of analyte detection scheme. With their small size, low power consumption, and high sensitivity, these v-shaped nanocantilever sensors can be easily integrated with emerging technologies such as energy harvesting and radio frequency identification devices giving rise to miniaturized next generation systems and components capable of working remotely over very long durations. This approach for the detection of electrical signals in neurons using an array of v-shaped nanocantilever probes can lead to significant advancement of neurology and neuro-science, by opening up non-traditional means for rapid and nanoscale characterization of neuronal signal propagation in-vivo.

For example, possible applications of the v-shaped nanocantilever probes can include nanoscale resonant sensors (VNC probes) for chemical, biological, radiological, and nuclear detection, uncooled infrared detectors and imagers, nanoscale probes in AFM for measurement of temperature profile, surface thermal conductivity, and surface potential of various analyte materials and devices, electron emitters under high field and used as ionization detectors, temperature controlled nanoscale filament to detect explosive vapors and other volatile organic chemicals based on their explosion points, very highly sensitive detectors for bio-molecules and bio-chemicals due to their surface electron accumulation, in arrays for very small electrical signals propagating in neurons simultaneously, etc. The VNC probes, when fabricated in the form of an array as shown in FIG. 6A can also be used as a novel method to probe intracellular proteins, DNA, and RNA. This can be achieved by utilizing the special V-shaped structure of the probe to puncture the cell membrane and using a functionalized coating on the VNC to detect appropriate molecules. This can enable much faster and more effective detection methodology for expediting drug discovery, and applications to various disease diagnosis and treatment, including Cancer and HIV.

EXAMPLES

I. Results of the Examples are as Follows

A. Nanowire Synthesis

InN nanowires were grown in a horizontal quartz-tube furnace through direct reaction between metallic In and $NH_3$ using Au catalyst (~20 Å thick) deposited by thermal evaporation. The growth was performed by VLS mechanism on $SiO_2$ (100 nm)/Si (100, $n^+$) using Au catalyst patterns. Two separate quartz tubes were used to carry $NH_3$ and $N_2$ (carrying In vapor) to prevent In vapors from pre-reacting with $NH_3$. The nominal temperature and pressure for the growth process was 700° C. and 50 Torr, respectively. The InN nanowires grew almost exclusively along the plane of the substrate in [110] and [1$\bar{1}$0] directions with a growth rate of ~30 μm/hr. Typical nanowires had diameters varying in the range of about 20 nm to about 50 nm and having lengths of about 5 μm to about 15 μm. SEM and TEM images of typical nanowires showed a smooth surface, uniform diameter, hexagonal structure, and expected chemical composition [from Energy Dispersive Spectra, EDS].

In general, the InN nanowires exhibited several interesting properties, which are discussed below:

Spontaneous and Forced Growth Redirections:

The InN nanowires were observed to suffer growth redirections either spontaneously, or when obstructed by a barrier, at angles that are multiples of 30°. This behavior is consistent with similar free energy of growth for a hexagonally symmetric lattice structure like in wurtzitic III-V Nitride compounds. However, it was found that the presence of two parallel barriers can make the nanowire suffer multiple growth redirections that can be quite symmetric and repeatable. For example, the deflection angles can be very close multiples of 30°. This highly significant property, which to our knowledge has never been observed for any other chemically synthesized NW or nanotube, provides a direct handle to control the NW growth and the geometry of the final nanostructure formed.

Guided Growth Along the Obstacle:

Although in most cases the nanowires changed their growth direction backward when obstructed, quite often it also grew along the barrier or follow its contour. Examples of barriers can be InN nanowire barriers, $SiO_2$ barriers, and $SiO_2$ trenches. Since the barrier templated growth is observed only in some instances, but not always, it is highly likely that there are specific conditions that favor this mode of growth. Identification of these conditions can lead to controlled and directed growth of the nanowires, which can then be exploited to fabricate desired nanostructures.

B. Electrical Characterization of the Nanowires:

Preliminary investigation of the electrical properties of the nanowires has been carried out by fabricating field effect transistors in a back-gated configuration using doped Si substrates as the back gate, and 100 nm $SiO_2$ layer as the gate dielectric. Electron beam lithography was used to define the source and drain metal contacts to the nanowires, which consisted of Ti/Al/Ti/Au layers (20/50/20/50 nm) deposited by thermal evaporation. A circular geometry for the outer ohmic contact was used to ensure contact with the nanowires which grew outward from the patterned catalyst spots. $I_d$-$V_d$ and $I_d$-$V_g$ curves were obtained for the nanowire FET. The gate current reduces smoothly on application of a negative gate bias indicating presence of n-type carriers in the nanowires. The electron mobility $\mu_e$ can be calculated from the $I_d$-$V_g$ curve using the relationship: $dI_D/dV_G=\mu_e(C/L^2)V_D$, where C and L are the capacitance and length of the nanowires, respectively. The mobility and carrier density obtained from these I-V characteristics were 700 $cm^2V^{-1}s^{-1}$ and $1.5\times10^{18}$ $cm^{-3}$, accounting for the fringing field due to nanowires curvature. These results, which represent the mean values for more than 20 devices studied, is a dramatic improvement in comparison to commonly measured data on InN nanowire FETs (mobility ~30 $cm^2/Vs$ and carrier density ~$10^{20}$ $cm^{-3}$). The low mobility and high carrier density observed so far precluded InN based devices from being thoroughly investigated for sensor applications, in spite of their highly interesting material properties. Another remarkable aspect of the preliminary studies is that they point to an increase in carrier mobility with a decrease in the NW diameter. Such a reverse correlation has also been reported recently, and attempts have been made to model it theoretically. These results are highly encouraging for the development of the VNC sensors (which will have diameter of ~20 nm), since a higher mobility will translate into higher sensitivity and reduced noise.

Figure 7:
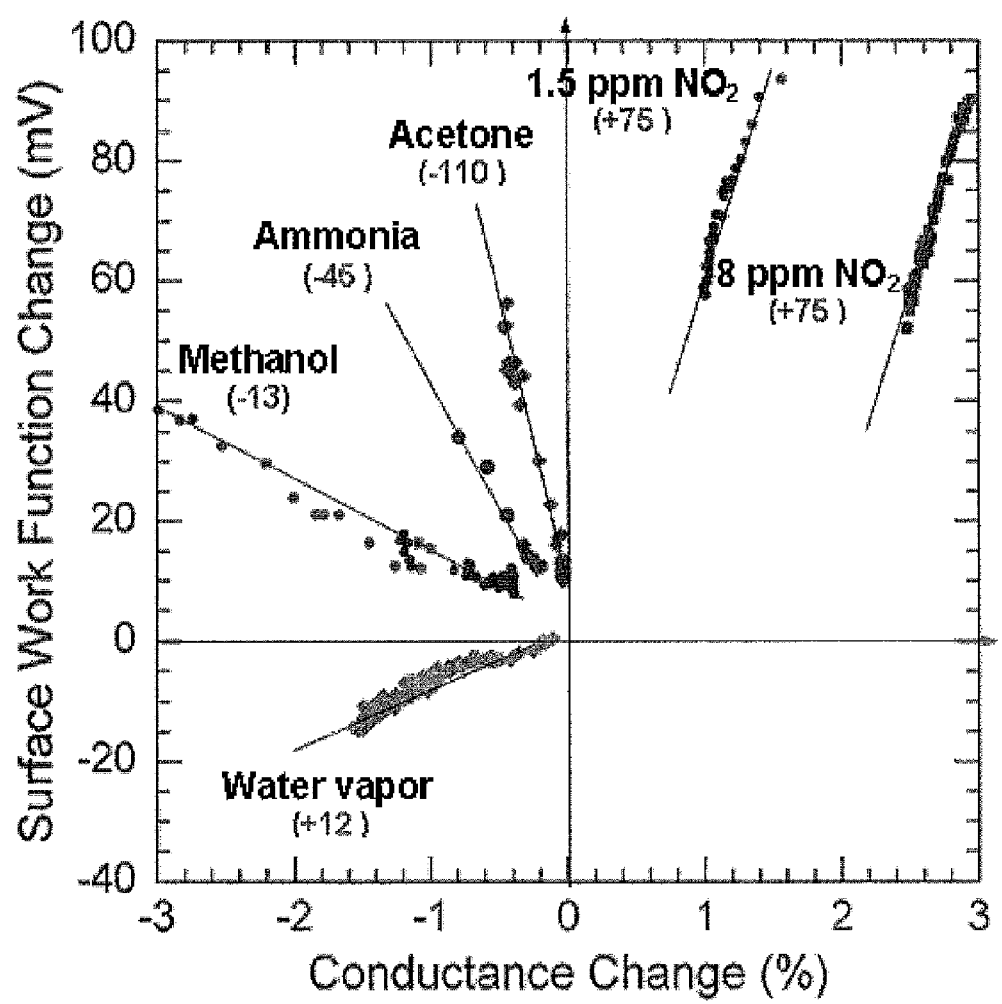
FIG. 7 shows two dimensional gradient signatures (2DGS) of various analytes according to the examples.

C. Bimodal Detection:

Prior results indicate that simultaneous measurement of SWF and conductivity changes ($\Delta\phi$ and $\Delta\sigma$) for a given functionalization layer can be utilized to eliminate their time dependence, and obtain a unique signature of the adsorbed analyte molecules based on the determination of their 2-dimensional gradient signatures $S_G$ given as: $S_G=\Delta\sigma/\Delta\phi$[17]. FIG. 7 shows a two-dimensional plot showing the changes in conductivity and SWF measured simultaneously (using a nanostructured graphite functionalization layer) in the two axes. Distinct slopes for different analyte molecules can be observed, which can be used to uniquely identify the molecules. This concept can be extended to include other parameters like capacitance, mass, or surface stress, leading to detection with even more certainty.

D. Design of the VNC Sensors:

The overall design of the VNC sensors allows for detection with very high sensitivity, low response time, and low power usage. Specifically our design goals are: (i) sensitivity (e.g., single molecule of analyte), (ii) response time: (e.g., less than about 100 μs for single molecule detection), and (iii) power for sensor operation (e.g., less than about 50 μW per VNC sensor). The lateral dimension of the sensor, "b" as shown in FIG. 1, is assumed to be about 2 μm, based on the requirements of optical lithography resolution and allowing some uncertainty in nanowire growth process. The resonant frequency $f_0$ and spring constant k of a V-shaped (triangular) cantilever is given as $f_0 \approx 0.323(k/M)^{1/2}$, where $$k\approx(Eh^3w)/2L^3)\cos\theta \text{ (for } w<<b\text{)} \quad \text{(formula 1)}$$

Here, E is the Young's modulus, and cantilever mass M=$\pi$ ($D^2/4$)(2l)$\rho$. Table 1 shows the initial design parameters, which may be optimized based on v-shaped nanocantilever sensor characterization, and their sensing performance, while Table 2 shows VNC parameters summary:

TABLE 1

| Parameters | Values |
|---|---|
| b | 2 μm |
| D | 20 nm |
| 2θ | 60° |
| E | 200 GPa |

TABLE 1-continued

| Parameters | Values |
|---|---|
| Q | 200 |
| ρ | 6.78 g/cm$^3$ |
| μ | 1000 cm$^2$/Vs |
| n | 10$^{18}$ cm$^{-3}$ |

TABLE 2

| Parameters | VNC Sensor |
|---|---|
| K | 2.68 × 10$^{-3}$ N/m |
| M | 8.51 × 10$^{-18}$ Kg |
| $\omega_0$ | 2π × 5.73 MHz |
| Δϕ | 35 μV @ 100 KHz |
| $P_{req}$ | 32 μW @ $V_{ac}$ = 5 V |

(i) Deflection Transduction:

The sensitivity of the VNC sensor was determined by the depletion of carriers in the nanowire due to the periodic movement of the probe under the applied ac voltage. Assuming a separation of 50 nm between the v-shaped nanocantilever and the surface, the change in carrier concentration (Δn) due to a deflection change in VNC-bias electrode separation (Δz) is given as:

$$\Delta n = (4\in_0 V_{ac}/q\pi Dz^2)\Delta z \quad \text{(formula 2)}$$

where $V_{ac}$ is the applied ac voltage. The depletion of the nanowire for z=1 nm (average for the entire cantilever) was 7.04×10$^{15}$ cm$^{-3}$. Thus, ΔR/R is about 1%, for a typical carrier density of 10$^{18}$ cm$^{-3}$ for the presently disclosed cantilevers. In addition to the depletion based changes, piezoresistive effects in InN can also change the resistivity in InN nanowires, especially due to its strong piezoelectric coefficients.

(ii) Noise:

The ultimate resolution of physical parameter changes as measured by a cantilever is dependent on the overall measurement noise. The major types of noise in a cantilever are: (i) Thermo-Mechanical (TM) noise, (ii) Johnson noise, and (iii) flicker noise. The flicker noise is usually not important at higher frequencies (>100 Hz), and can be neglected for the presently disclosed VNC sensors. The root mean square (rms) value of the TM displacement noise of the tip $<x_{tm}^2>^{1/2}$ is given as:

$$<x_{tm}^2>^{1/2} = (4Qk_B TB/k\omega_0)_{1/2} \quad \text{(formula 3)}$$

where Q is the quality factor, $k_B$ is Boltzmann's constant, and T is absolute temperature. Using the dimensions of the VNC as shown in Table 1, we get $<x_{tm}^2>^{1/2}$=1.85 nm for a measurement bandwidth B=100 KHz. The Johnson voltage noise in a resistor R is given as: $<V_j^2>^{1/2}=(4k_B TRB)^{1/2}$. At room temperature, for B=100 KHz, and R=0.8 MΩ, $<V_j^2>^{1/2}$=36.4 μV. The voltage noise $<V_j^2>^{1/2}$ is related to the corresponding displacement noise $<x_j^2>^{1/2}$ of the cantilever tip by: $<V_j^2>^{1/2} \approx (4\in_0 V_{ac}^2/nq\pi Dz^2)<x_j^2>^{1/2}$. For $<V_j^2>^{1/2}$=36.4 μV, the corresponding displacement noise $<x_j^2>^{1/2}$=0.1 Å at B=100 KHz, which is negligible compared to the TM noise.

(iii) SWF and Stress Change Measurements:

The amplitude a of a resonant VNC sensor is dependent on the sinusoidal applied force $F_\omega$, and the quality factor Q by the relationship: a=QF$_\omega$/k. For an applied voltage $V_{ac}$ sin ωt, $F_\omega$ is given as: $F_\omega = (\partial C/\partial z)(\delta\phi+\Delta\phi)V_{ac}$ sin ωt, where δϕ is the SWF difference between the tip and the biasing electrode (controlled by an external dc bias), and Δϕ is the change in SWF due to adsorption of molecules on the surface. Then the change in amplitude Δa is given as [26], [27]:

$$\Delta a = (Q/k)(\partial C/\partial z)(\Delta\phi)V_{ac} \quad \text{(formula 3)}$$

For the values of Q and k from Tables 1 and 2, and assuming z=50 nm, Δϕ=0.1 mV, and $V_{ac}$=5 V, we find a=5.28 nm. Considering the binding site density on the surface as 10$^{13}$ cm$^{-2}$ (this is more conservative than what has been used for Δϕ transient modeling), the total number of binding sites in the interaction area of the VNC is 10$^{13}$ cm$^{-2}$×4×10$^{-4}$ cm×20× 10$^{-7}$ cm=8000. Assuming Δϕ for a single molecular attachment is a few tenths of a V (typical for $H_2$, $NO_2$), the average SWF change for the entire area is ~50 μV. This results in an amplitude change of 2.64 nm which is larger than the noise level of 1.85 nm, indicating that single molecular binding events are possible to detect.

(iv) Power Requirement:

The operational power requirement of the cantilever is made of two components: one to maintain continuous oscillation $P_{osc}$, and the other to transduce the deflection $P_{trans}$. $P_{osc}$ can be calculated from the kinetic energy $E_{KE}$, quality factor Q, and the resonant frequency $\omega_D$ from the relationship: $P_{osc}=2\pi E_{KE}/(Q\omega_0)$. The kinetic energy $E_{KE}$=½I ω$^2$, where I is the moment of inertia, and ω is the angular frequency. Using dimensions from Table 1, $P_{osc}$=0.2 μW. $P_{trans}$ is much higher than that, and comes out to be $V_{ac}^2$/R=31.25 μW. Of course, this can be reduced by reducing the $V_{ac}$, however, the sensitivity will also be reduced.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention.

What is claimed:

1. A sensor, comprising:
   an n+ layer;
   a layer of silicon oxide on a portion of the n+ layer to form an uneven surface where the layer of silicon oxide defines a thicker region than an exposed portion of the n+ layer;
   a first metal contact on the layer of silicon oxide;
   a second metal contact on the layer of silicon oxide;
   a v-shaped nanowire extending over the exposed portion of the n+ layer, wherein the v-shaped nanowire defines a first arm extending from a first base contacting the first metal contact, wherein the first arm extents over the exposed portion of the n+ layer for a first length, and wherein the v-shaped nanowire defines a second arm extending from a second base contacting the second metal contact, wherein the second arm extents over the exposed portion of the n+ layer for a second length,
   the first arm and the second arm being connected together at an apex to form the v-shaped nanowire, wherein the apex is positioned over the exposed portion of the n+ layer, and wherein the v-shaped nanowire comprises indium and nitrogen.

2. The sensor as in claim 1, wherein the first arm has an average diameter of about 10 nm to about 50 nm, and wherein the second arm has an average diameter of about 10 nm to about 50 nm.

3. The sensor as in claim 1, wherein the first arm has an average diameter of about 20 nm to about 40 nm, and wherein the second arm has an average diameter of about 20 nm to about 40 nm.

4. The sensor as in claim 1, wherein the first length and the second length are substantially equal.

5. The sensor as in claim 1, wherein the first length is about 2 μm to about 5 μm.

6. The sensor as in claim 1, wherein the first arm and the second arm are connected together at the apex at an angle of about 30° to about 75°.

7. The sensor as in claim 1, wherein the first nanowire and the second nanowire are connected together at the apex forming an angle that is about 35° to about 60°.

8. The sensor as in claim 1, wherein the first base and the second base are spaced apart from each other at a base distance, wherein the base distance is about 1 μm to about 5 μm.

9. The sensor as in claim 1, further comprising:
a substrate, wherein the n+ layer is positioned on the substrate.

10. The sensor as in claim 9, wherein the substrate is a p-type substrate.

11. The sensor as in claim 9, wherein the substrate is a p-type Si substrate.

12. The sensor as in claim 1, wherein the n+ layer defines a functionalized surface over the exposed portion.

13. The sensor as in claim 12, wherein the functionalized surface is configured to bind to an analyte.

14. The sensor as in claim 13, wherein the analyte comprises a virus, a protein, DNA, RNA, or a volatile organic species.

15. The sensor as in claim 1, wherein the v-shaped nanowire comprises InN.

16. The sensor as in claim 1, wherein the v-shaped nanowire comprises a shell layer positioned around a core layer.

17. The sensor as in claim 16, wherein the shell layer comprises $In_2O_3$.

18. The sensor as in claim 16, wherein the core layer comprises InN.

* * * * *